United States Patent [19]

Chiurco et al.

[11] Patent Number: 4,860,748
[45] Date of Patent: Aug. 29, 1989

[54] THERMAL PATTERN GENERATOR FOR PAIN RELIEF

[75] Inventors: Anthony A. Chiurco, Princeton, N.J.; Michael G. Littman, Philadelphia, Pa.

[73] Assignee: Thermapeutics, Inc., Princeton, N.J.

[21] Appl. No.: 159,237

[22] Filed: Feb. 23, 1988

[51] Int. Cl.$^4$ ................................................. A61F 7/00
[52] U.S. Cl. ..................................... 128/399; 128/402
[58] Field of Search ............. 128/399, 402, 362, 303.1

[56] References Cited

U.S. PATENT DOCUMENTS

| | | | |
|---|---|---|---|
| 3,132,688 | 5/1964 | Nowak | 128/399 |
| 4,585,002 | 4/1986 | Kissin | 128/399 |
| 4,741,338 | 5/1988 | Miyamae | 128/399 |

FOREIGN PATENT DOCUMENTS 577028 10/1977 U.S.S.R. ............................... 128/399

797686 1/1981 U.S.S.R. ............................... 128/399

Primary Examiner—Francis Jaworski
Assistant Examiner—John C. Hanley
Attorney, Agent, or Firm—Richard C. Woodbridge

[57] ABSTRACT

An array of Peltier-effect thermoelectric tiles are controlled by a microprocessor so as to produce a repeatable series of temperature patterns or sequences on the skin adjacent to the area of pain. The series can be modified by selecting between one and m different pre-programmed thermal patterns or sequences by the appropriate setting of a m-toggle switch bank. The hot intensity, cold intensity and time delay between sequences can also be selected. The period between temperature changes is greater than one minute. A variety of different pain soothing sequences can be generated including checkerboard patterns, hot and cold waves, alternating left and right side temperature changes, etc.

18 Claims, 12 Drawing Sheets

FIG. 6A
SEQUENCE #1
[HOT- ALL ON/ALL OFF]

FIG. 6B
SEQUENCE #2
[COLD- ALL ON/ALL OFF]

FIG. 6C
SEQUENCE #3
[PAIR- ALL ON/ALL OFF]

FIG. 6D

SEQUENCE #4
[2 COLD/REST OFF—
COLD WAVE]

FIG. 6E

SEQUENCE #5
[LEFT HOT/RIGHT COLD
WITH REVERSAL]

FIG. 6F

SEQUENCE #6
[ONE TILE ON LEFT COLD/
ONE TILE ON RIGHT HOT
THEN REVERSED- HOT/COLD
WAVE WITH REVERSED]

*FIG. 6G*

SEQUENCE #7
[CHECKER BOARD]

*FIG. 6H*

SEQUENCE #8
[CHECKER BOARD/WAVE
COMBINATION WITH REVERSAL]

*FIG. 6I*

SEQUENCE #9
[RANDOM]

FIG. 6J

SEQUENCE #10
[ALTERNATE PARTS HOT AND COLD]

FIG. 6K

SEQUENCE #11
[ALTERNATE HOT/COLD PAIR WAVE WITH REVERSAL]

FIG. 6L

SEQUENCE #12
[HIGH RIGHT/LOW LEFT HEAT WAVE]

FIG. 6M

SEQUENCE #13
[HIGH RIGHT/LOW LEFT
COLD WAVE]

THERMAL PATTERN GENERATOR FOR PAIN RELIEF

BACKGROUND OF THE INVENTION

1. Field of the Invention

The present invention relates to a method and apparatus for producing a repeatable series of temperature patterns on the skin of a pain sufferer by selectively and independently controlling the heating and cooling of Peltier-effect thermoelectric devices in an array with a programmable microcomputer.

2. Related Prior Art

The ability to decrease pain through the use of heat and cold is generally known. The patent literature includes several disclosures of devices which apply either heat and/or cold to control pain, see for example, U.S. Pat. Nos. 3,168,895 and 4,294,254. The following reference articles also describe useful background information:

ICE MASSAGE AND TRANSCUTANEOUS ELECTRICAL STIMULATION; COMPARISON OF TREATMENT FOR LOW BACK PAIN

R. Melzack, M. E. Jeans, J. G. Stratford and R. C. Monks,
Pain, 9:209-217, 1980, Elsevier/North-Holland Biomedical Press

EFFECTS OF LOCAL HYPOTHERMIA ON REFLEX AND VOLUNTARY ACTIVITY

Sara A. Mecomber, B. S. and Richard M. Herman, M.D., Physical Therapy 51(3): 271-281, March 1971

ICE THERAPY IN SPASTICITY

Karl Hartirksen, Acta Neurol Scandinav, 38(3): 79-84, 1982

ACTION OF COLD ON SPASTICITY

Osvaldo Miglietta, M.D., F.A.C.P. American Journal of Physical Medicine 52(4): 98-205, August, 1973

THE THERAPEUTIC USE OF COLD

John M. Mennell, M.D. Journal of the American Osteopathic Association, 74(12): 1146-1158, August 1975

A REVIEW OF CRYOTHERAPY

Jane E. Olson, M.A. Physical Therapy, 52(8): 840-953, August 1972

THERAPEUTIC HEAT AND COLD

Justis F. Lehman, M.D., C. Gerald Warren, M.P.A. and Stewart M. Sham, M.D. Clinical Orthopedics and Related Research 99(3-4): 207-245, 1974

THERAPEUTIC HEAT AND COLD

Justus F. Lehman, Barbara deLateur Principles in Physical Medicine and Rehabilitation in the Musculoskeletal Diseases, Grune and Stratton, Inc., Phila. 1986 pp 61-101

GENERAL PRINCIPLES OF THERMOTHERAPY

G. Keith Stillwell in Therapeutic Heat and Cold, D. Sidney Herman Licht and Herman L. Kornentez, Chapter 7, pp. 232-239, Pubs. E. Licht New Haven, 1965

PHYSIOLOGICAL RESPONSES TO HEAT AND COLD

Sydney Fischer and Sidney Solomon, Chapter 4, pp. 126-159, Pubs. E. Licht, New Haven, 1965, Second Edition.

Several prior art devices employ Peltier effect devices for producing hot and cold temperature changes on or in the human body. In particular, note U.S. Pat. Nos. 2,938,356; 3,207,159; 3,295,522; 3,618,590; 4,585,002; Re. No. 26,276 and French Patent No. 2,579,888. In general the foregoing Peltier effect devices employ one or more tiles acting in unison, and typically at relatively high repetition rates, to apply heat and cold to a part of the body. U.S. Pat. No. 4,585,002 entitled METHOD AND APPARATUS FOR TREATMENT OF PAIN BY FREQUENTLY ALTERNATING TEMPERATURE STIMULATION, is typical in that it discloses a pain treatment device in which the Peltier thermoelectric units are turned on and off as a group with a frequency in the range of 5 to 30 seconds, and preferably with a period shorter than one minute.

The invention set forth in this disclosure is different from the devices such as described in U.S. Pat. No. 4,585,002 in that the period of the temperature change is greater than one minute and also in that a variety of different temperature patterns are applied to the affected area. The variety of patterns is believed preferable to the predictable and monotonous application of heat and cold in that adaptation is not likely.

Insofar as understood, none of the prior art inventions teach or suggest the present invention

SUMMARY OF THE INVENTION

Briefly described the invention comprises a device for producing a repeatable series of temperature change patterns or sequences on the skin so as to decrease pain. A microcomputer is attached to an array of Peltier effect tiles arranged in an organized manner—for example, two rows of four tiles each. The array of Peltier tiles can be placed against the lower back in order to reduce lower back pain or on the forehead in the case of headaches or the like. A program selector includes between one and m toggle switches in a bank that permits the user to select a series of temperature change patterns or sequences. The program selector is connected to the microcomputer which scans the setting of the toggle switches and controls the array of Peltier effect tiles to produce selected output patterns in series. It has been found that pattern changes with a period greater than one minute in this context appear to be quite effective. The program selector switches might be set, for example, to choose a wave pattern, then a checkerboard pattern, then an alternating right and left side pattern, etc. Once the series has been run, it is repeated indefinitely until the unit is either turned off or the program selector switches are modified to produce a different series of patterns. The temperature extreme of the heating and cooling of the Peltier effect tiles is controlled by a heat intensity control and a cold intensity control connected to the microcomputer respectively. The delay between sequences is controllable by a delay control unit.

These and other features of the present invention will be more fully understood by reference to the following drawings.

DETAILED DESCRIPTION OF THE PREFERRED EMBODIMENT

During the course of this description like numbers will be used to identify like elements according to the different views which illustrate the invention.

Figure 1:
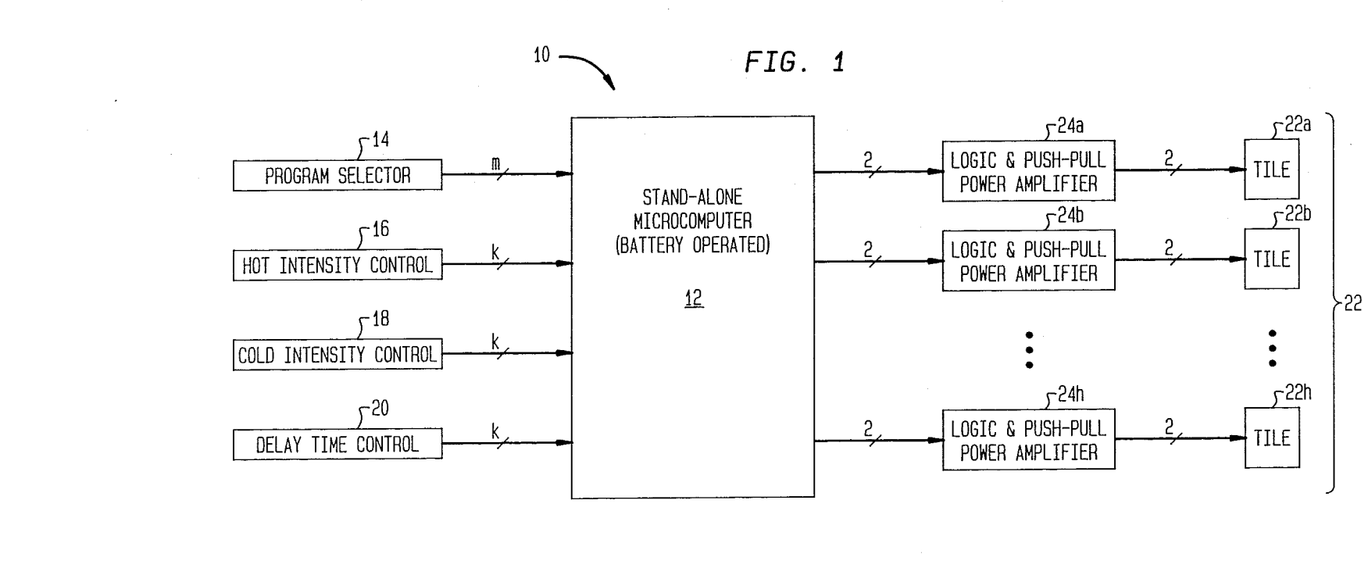
FIG. 1 is a block schematic diagram of the preferred embodiment of the invention.

The preferred embodiment of the invention 10 is illustrated in the block diagram of FIG. 1. A portable, battery operated, microcomputer 12 is connected to and controlled by a program selector 14, a hot intensity control 16, cold intensity control 18 and delay time control 20. Microcomputer 12 is also connected to 8 control circuits containing digital logic and push-pull power amplifiers 24A-24H which in turn are respectively connected to 8 Peltier-effect tiles 22A-22H. The Peltier tiles 22A-22H are connected in an array 22 similar to that shown, for example, in FIGS. 4A and 4B. According to the preferred embodiment of the invention the microcomputer 12 comprises a R6500/1EAB3 microcomputer manufactured and sold by Rockwell International.

Figure 2:
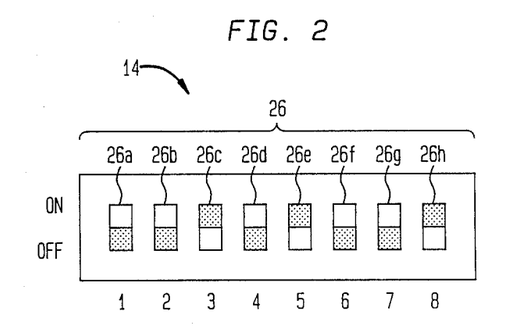
FIG. 2 illustrates the setting of the toggle switches on the program sequence selector with Program Nos. 3, 5 and 8 shown selected.

The program selector 14 is shown in detail in FIG. 2. Each of the 8 toggle switches 26A-26H in the bank 14 is employed to select one of a group of different temperature sequences which may be generated on the tiles 22A-22H.

As used in this disclosure the term "pattern" is used to describe a fixed thermal pattern at a specific point in time (e.g. at the 16th second from the beginning of operation, i.e. second zero) and "sequence" means the thermal pattern over time which may or may not change as shown in FIGS. 6A-6M. The term "series" is used to define a string of one or more connective sequences (e.g. sequences 3, 5 and 8 as shown in FIGS. 2, 3 and 4C) which preferably repeats after it gets to the last sequence in a string.

Figure 3:
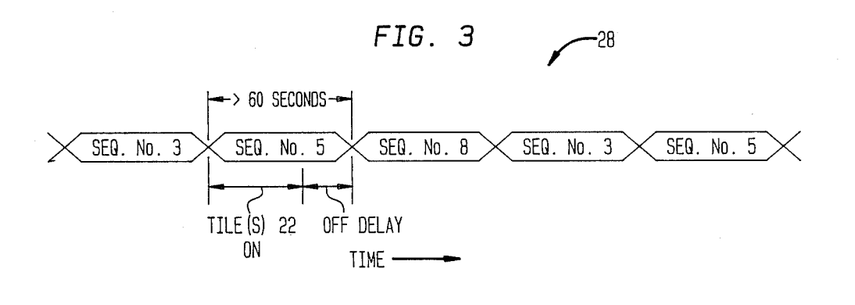
FIG. 3 illustrates a typical series of temperature change patterns or sequences produced by the toggle switch settings on the program selector of FIG. 2.
Figure 4A:
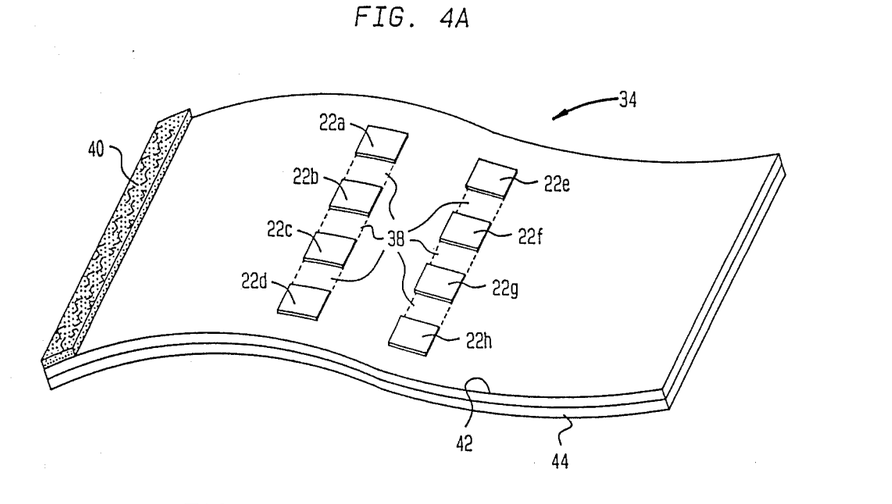
FIG. 4A is a perspective view of an array of Peltier effect tiles attached to a corset for application to the lower back of a patient.
Figure 4B:
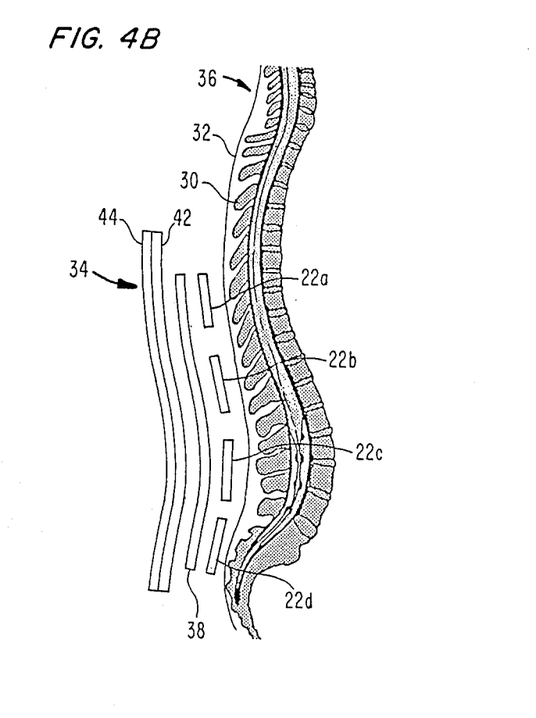
FIG. 4B is a cross-sectional, sagittal plane view of the Peltier-effect tiles applied to the lower back of the patient shown in FIG. 4A.
Figure 4C:
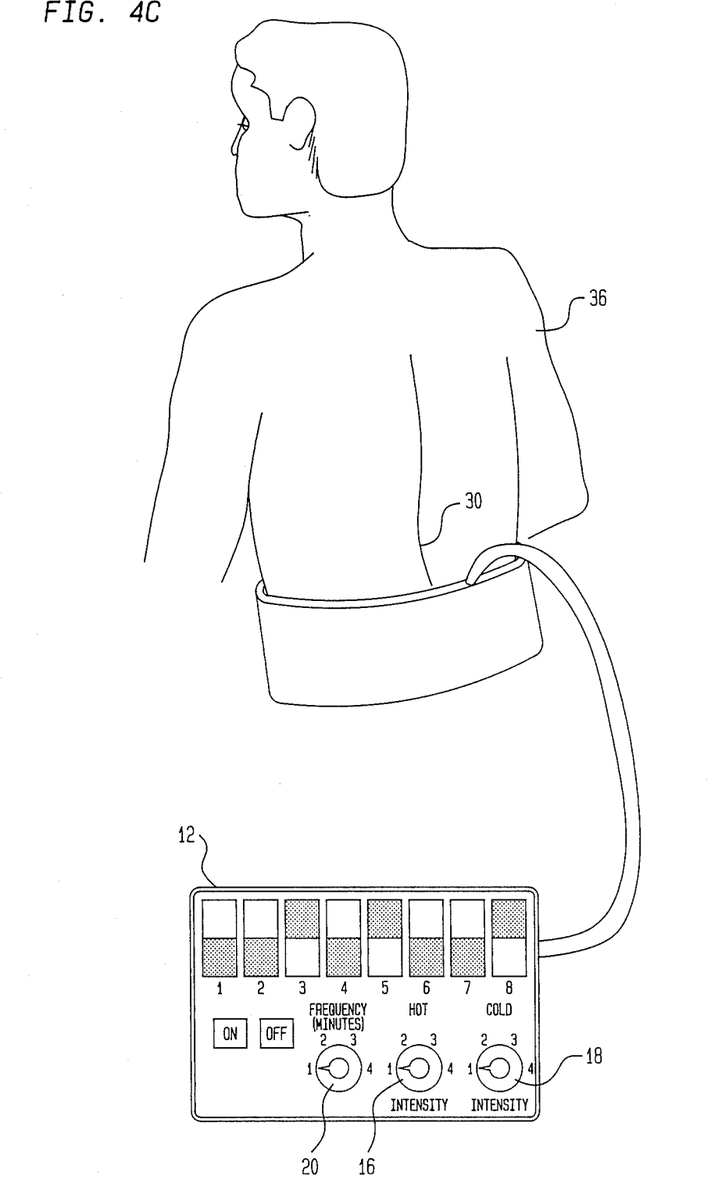
FIG. 4C illustrates the microcomputer control console electrically attached to the corset applied to the lower back of a patient.

A typical repeating series 28 of different temperature patterns or sequences is illustrated in FIG. 3. Temperature series 28 is applied to the skin of a user through tile 22A-22H as shown in FIGS. 4A and 4B. A corset 34 holds the tiles 22A-22H against the skin 32 adjacent the lower back 30 of the pain sufferer 36 as shown in FIG. 4C. Corset 34 comprises an interior plastic foam layer 42 which supports thermoelectric tiles 22a-22h and is covered by an exterior elastic band 44. A hook and loop fastener material 40 such as Velcro ® is employed to attach the two ends of the corset 34 together. The selectivity of the attachment material 40 and the elasticity of the outer layer 44 make it possible for the corset 34 to accommodate patients 36 having different sized waist measurements.

Initially the patient 36 gets into the corset 34 which contains a plurality of thermoelectric tiles 22A-22H arranged in a regular 2×4 array. The thermoelectric tiles 22A-22H are positioned so as to be in direct contact with the skin 32 adjacent to the pain area. The invention 10 can also be employed to relieve pain in other areas such as the head in the case of headaches, neck pain, joint pain and the like. Patient 36 initially selects between 1 and m preprogrammed thermal sequences by the appropriate setting of the toggle switches 26A-26H of program selector 14 as illustrated in FIGS. 2 and 4C. Patient 36 also selects the high and low temperature limits as set by the hot intensity control 16 and the cold intensity control 18 respectively as well as a delay time on delay time control 20. Delay time control 20 controls the time during which all of the tiles 22A–22H are turned off. Hot intensity control 16, cold intensity control 18 and delay time control 20 may comprise three K-elements toggle switch banks or three $2^k$-position rotary switches. In the embodiment shown in FIGS. 5A–5C K=2 and the control comprises three, two-switch toggle pairs.

When powered the internal program of microcomputer 12 reads the hot intensity control 16, the cold intensity control 18 and the delay control 20 and sets internal parameters according to appropriate look-up tables. The microcomputer then proceeds in sequence to interrogate the state of each of the m (in this case 8) switches 26A–26H in the program selector 14 as illustrated in FIGS. 1 and 2. If a switch 26A–26H is on, then one cycle of the corresponding thermal sequence or pattern will be applied to the tiles 22A–22H. If a switch 26A–26H is off, the next switch will be interrogated immediately. For example, if switch 26D is off, then switch 26E will be interrogated next. After all of the switches 26A–26H have been interrogated, the time series is repeated indefinitely.

The following is a specific example of the sequence selection process. As shown in FIG. 2, switches No. 3, 5, and 8 (26C, 26E and 26H) of an 8-switch program selector 14 are turned on. The microcomputer 12 first interrogates switch No. 1 (26A). Since switch No. 1 (26A) is off, the microcomputer 12 immediately proceeds to switch 2 (26B). Switch 2 (26B) is also off so the microcomputer 12 next tests switch 3 (26C). Switch 3 (26C) is on so the program jumps to the sequence subroutine represented by switch 3 which applies a preprogrammed thermal temporal-spatial pattern to the array of tiles 22A–22H. In this case, for example, sequence No. 3 as shown in FIG. 3 and C, might be a heat wave followed by a delay. When a given thermal sequence is completed control is passed back to the microcomputer 12 which resumes by testing the state of switch No. 4 (26D) and so forth. The series of patterns or sequences 28 produced by the setting of the switches in FIG. 2 is illustrated in FIG. 3. Since the minimum delay is 60 seconds, all sequences last longer than one minute. It is also true generally that within a given sequence the temperature of any specific tile 22A–22H is never reversed (that is hot-to-cold or cold-to-hot) so that thermal gradients are never reversed more often than once per minute.

The preferred operating range of tiles 22A–22H is 19 degrees celsius to 44 degrees celsius with a preferred cold temperature of 19 degrees celsius and a preferred hot temperature of about 41 degrees celsius.

From the foregoing example it should be clear that the patient 36 has the unique ability to select different patterns or sequences of hot or cold cutaneous thermal stimulation simply by changing the switch settings of the program selector 14. This feature is deemed essential to avoid adaptation to thermal stimulus.

According to the preferred embodiment 10 the entire device is powered by rechargeable batteries so that it is portable.

Other examples of program sequences 28 are best demonstrated in a low-back model unit 34 which involves 8 tiles 22A–22H arranged in a 2×4 rectangle lining the paraspinal muscles of the lower back 30 as shown in FIGS. 4A and 4B. Eight sequences are possible given the eight switches 26a–26h illustrated in FIG. 2. These eight sequences might be taken from the following list of thirteen repeatable sequences that are not necessarily intended to be exhaustive examples of the sequences that might be employed.

Sequence No. 1. (FIG. 6A) All tiles 22 are hot for 10 seconds (at various levels of heat as determined by the hot intensity control 16), then off for a delay time greater than 60 seconds.

Sequence No. 2. (FIG. 6B) All tiles 22 are cold for 10 seconds (at various levels of cold as determined by the cold intensity control 18), then off for a delay time greater than 60 seconds.

Sequence No. 3. (FIG. 6C) The lower two tiles 22D and 22H hot for 10 seconds, then the next pair of tiles 22C and 22G hot (with the lower ones 22D and 22H turned off) for 10 seconds, then the next pair 22B and 22F on (i.e. hot) for 10 seconds (with all others off) and finally the top pair 22A and 22E hot for 10 seconds, followed by delay time of more than 30 seconds. This sequence is referred to as a heat wave.

Sequence No. 4. (FIG. 6D) A cold wave generated in a manner similar to the heat wave described in sequence 3 above.

Sequence No. 5. (FIG. 6E) All tiles on the left 22A–22D are hot while the tiles on the right 22E–22H are cold for 10 seconds, then a delay of 60 seconds, then reversal of above pattern, i.e. tiles on left cold, right hot, then a subsequent delay.

Sequence No. 6. (FIG. 6F) A similar to No. 5 but as a wave, then a delay of 60 seconds, then reversal of the pattern, then a subsequent delay.

Sequence No. 7. (FIG. 6G) A checkerboard pattern of hot and cold tiles alternatively (e.g. 22A, 22C, 22F and 22H on hot with 22B, 22D, 22E and 22G on cold) for 10 seconds and then a delay of 60 seconds, then a reversal, then another delay.

Sequence No. 8. (FIG. 6H) A checkerboard pattern similar to No. 7 above except in the form of a wave, then delay, then reversal, then another delay.

Sequence No. 9. (FIG. 6I) A random pattern in which the hot and cold tiles are turned on intermittently and do not change thermal direction more frequently than once per 60 seconds.

Sequence No. 10. (FIG. 6J) Alternate pairs of tiles are hot and cold, followed by a 60 second delay, followed by a reversal o the pattern, then a subsequent delay.

Sequence No. 11. (FIG. 6K) An alternating hot/cold pair wave, followed by a 60 second delay, followed by a reversal, then another delay.

Sequence No. 12. (FIG. 6L) A pair of heat waves starting at opposing ends and on opposing sides of said array followed by a 60 second delay.

Sequence No. 13. (FIG. 6M) A cold wave, similar to sequence No. 12 above, in which a pair of cold waves starts from opposing ends and opposing sides of said array, followed by a 60 second delay.

Figure 5A:
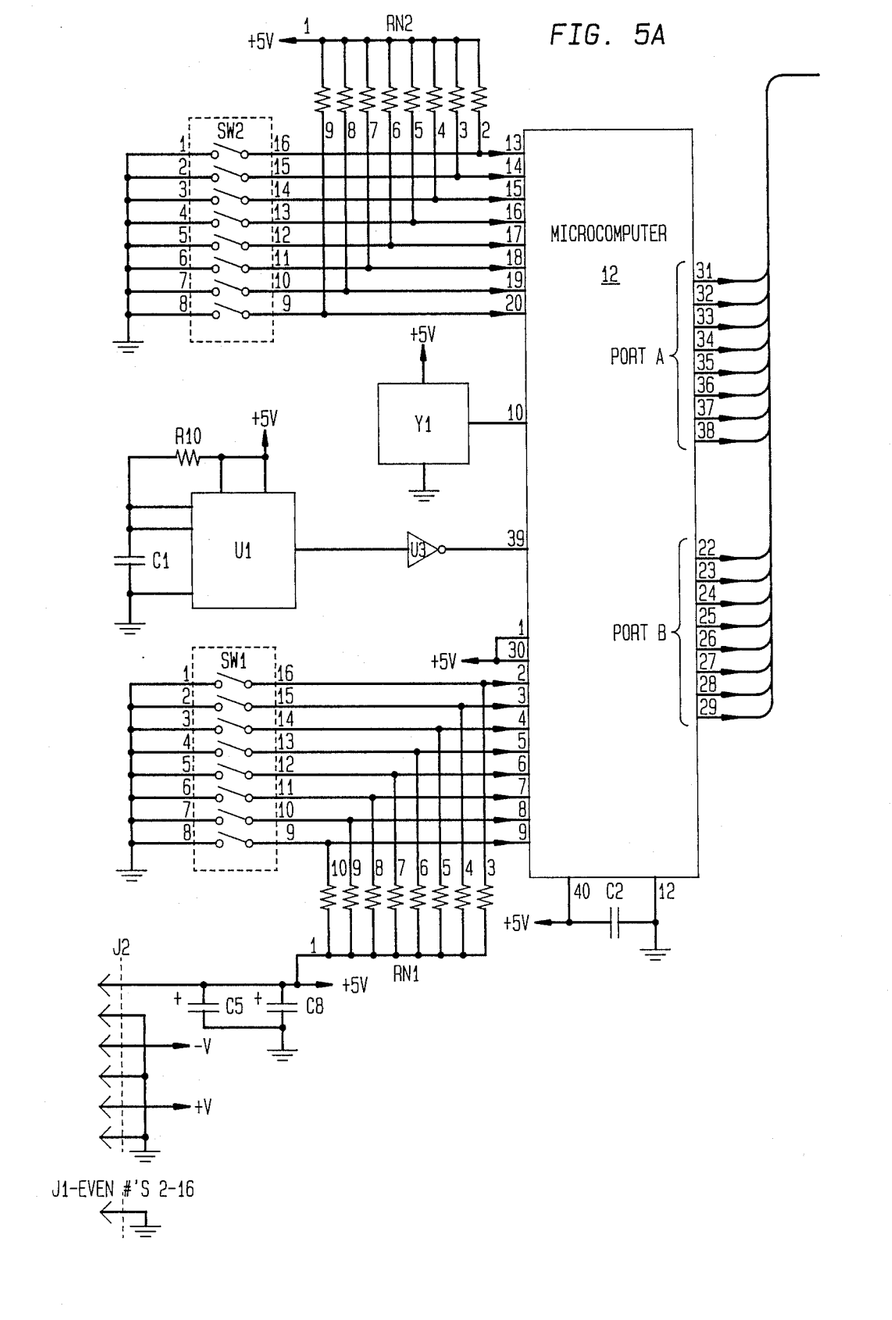
FIGS. 5A-5C comprise a detailed schematic view showing the specific elements which comprise the invention more generally illustrated in FIG. 1.
Figure 5B:
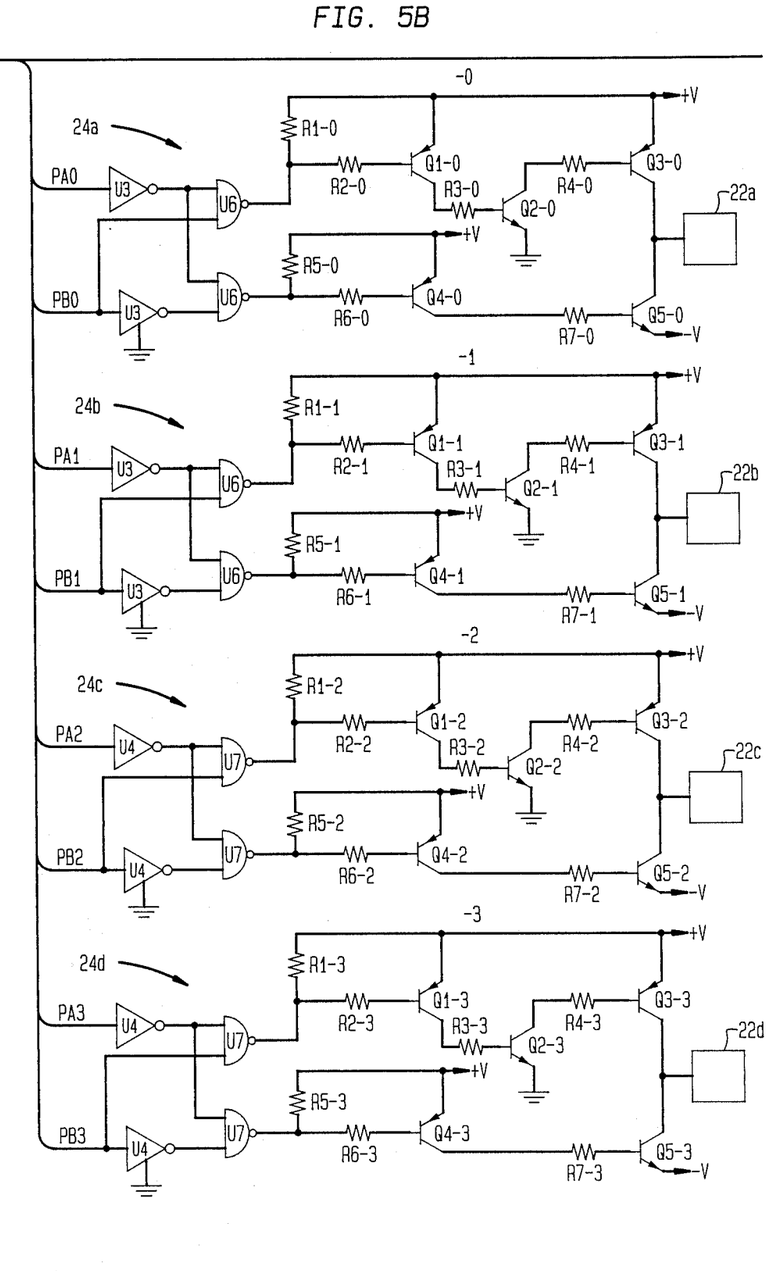
Figure 5C:
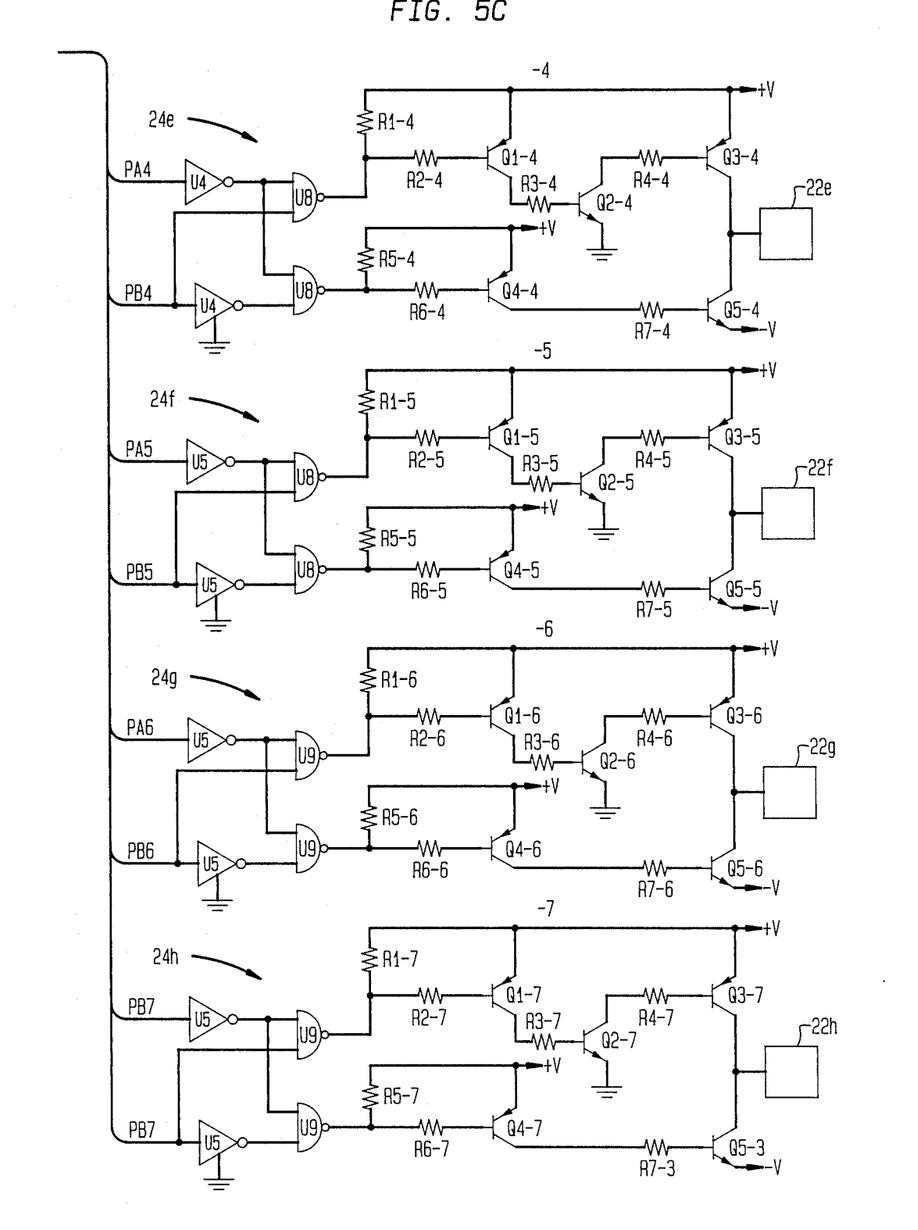
Figure 6A:
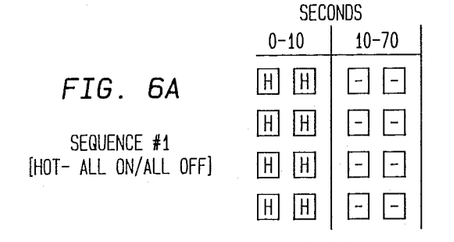
FIG. 6A illustrates sequence No. 1 in which all of the tiles are hot, followed by a delay in which all tiles are turned off.
Figure 6B:
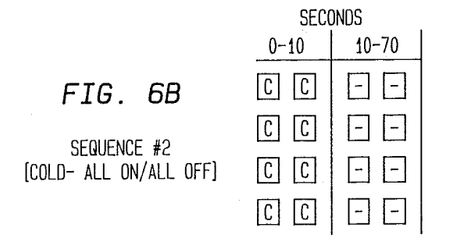
FIG. 6B illustrates sequence No. 2 in which all of the tiles are cold, followed by a delay in which all the tiles are off.
Figure 6C:
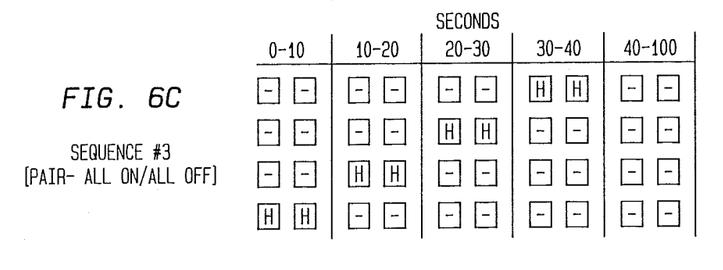
FIG. 6C illustrates sequence No. 3 in which a pair of adjacent tiles are hot while the rest of the tiles are off and wherein the hot pair moves up the array like a wave, followed by a delay during which times all tiles are off.
Figure 6D:
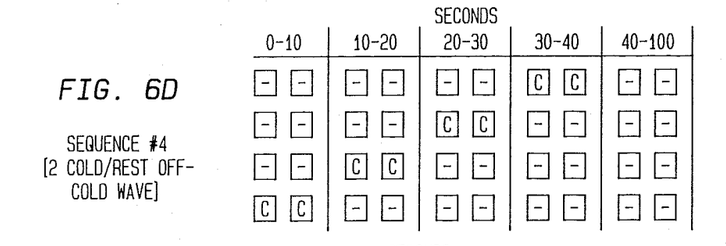
FIG. 6D illustrates sequence No. 4 which is similar to sequence No. 3 in FIG. 6C wherein a pair of tiles are cold while the other tiles are off and in which the cold pair travels up the array like a wave, followed by a delay.
Figure 6E:
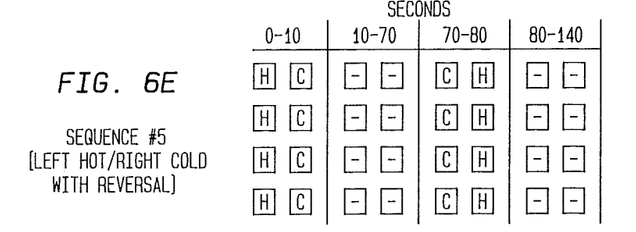
FIG. 6E illustrates sequence No. 5 in which 11 of the tiles on the left are hot, and all of the tiles on the right are cold, followed by a delay, followed by a reversal of the pattern, followed by a subsequent delay.
Figure 6F:
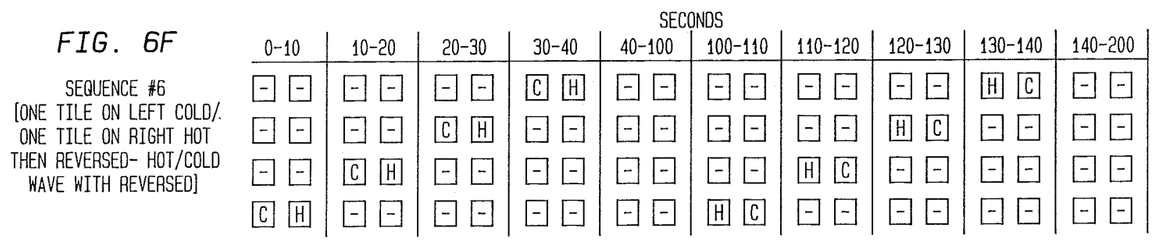
FIG. 6F illustrates sequence No. 6 in which one tile on the left is cold, and one tile on the right is hot, which advances as a wave, followed by a delay, followed by a reversal of the pattern, followed by a subsequent delay.
Figure 6G:
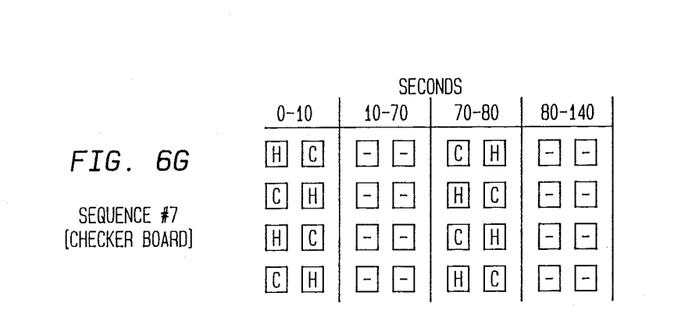
FIG. 6G illustrates sequence No. 7 in which the hot and cold tiles form a checkerboard pattern, followed by a delay during which all the tiles are off, followed by a reversal of the pattern, followed by a subsequent delay.
Figure 6H:
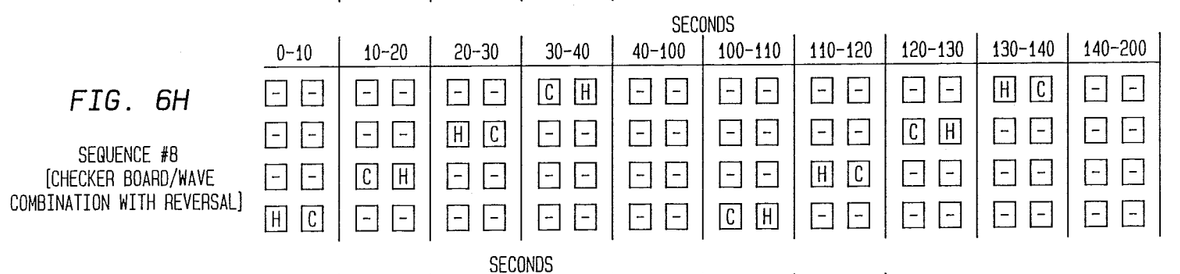
FIG. 6H illustrates sequence No. 8 which comprises a checkerboard/wave combination, followed by a delay, followed by a reversal of the pattern, followed by a subsequent delay.
Figure 6I:
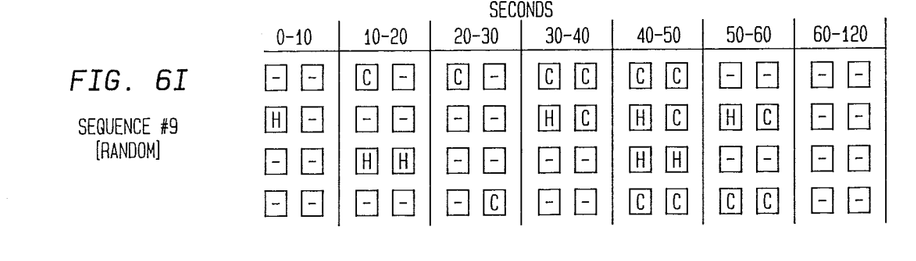
FIG. 6I illustrates sequence No. 9 which comprises a random pattern, but wherein the pattern of hot and cold does not change direction more often than once every 60 seconds, followed by a delay.
Figure 6J:
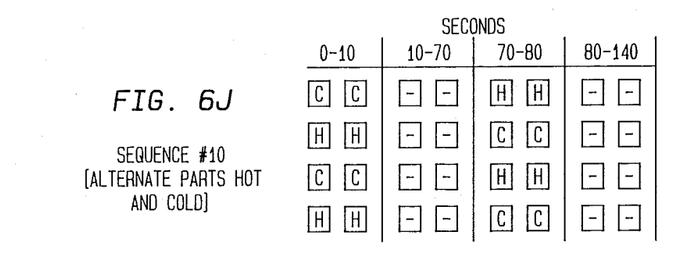
FIG. 6J illustrates sequence No. 10 in which alternate pairs of tiles are hot and cold, followed by a delay, followed by a reversal of the pattern, followed by a subsequent delay.
Figure 6K:
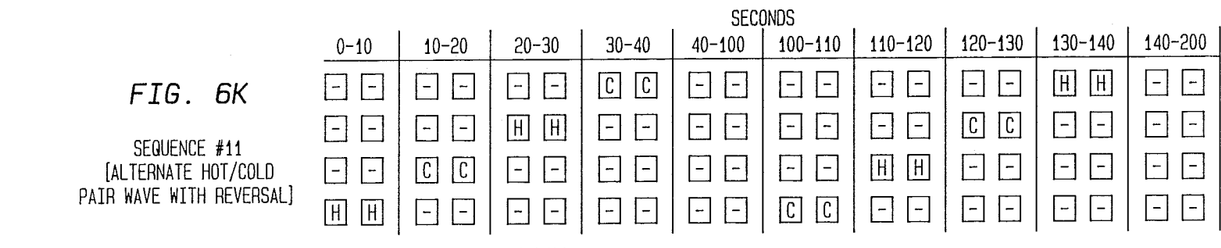
FIG. 6K illustrates sequence No. 11 in which alternate pairs of tiles become hot and then cold, advancing as a wave, followed by a delay, followed by a reversal of the pattern, followed by a subsequent delay.
Figure 6L:
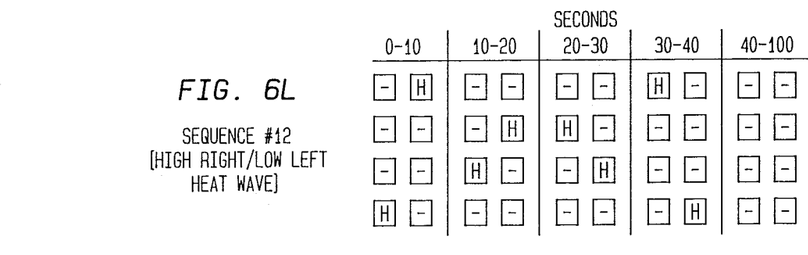
FIG. 6L illustrates sequence No. 12 which comprises opposing waves starting with the tiles in the lower left hand corner and upper and right hand corner hot.
Figure 6M:
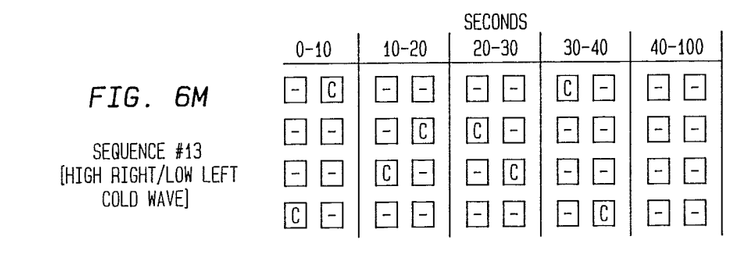
FIG. 6M illustrates sequence No. 13 which comprises a wave starting with the tile in the lower left hand corner and the tile in the upper right hand corner cold.

FIGS. 5A–5C comprise a detailed electronic schematic of the elements which comprise the preferred embodiment of the present invention 10. The major elements which comprise the invention are identified in the table below.

TABLE OF ELEMENTS

| Element | Description |
| --- | --- |
| J2 | Connector, 6 pin |
| J1 | Connector, 16 pin right angle |

TABLE OF ELEMENTS-continued

| Element | Description |
| --- | --- |
| Q5 | NPN Transistor, (To-220); Model No. MJE3055T |
| Q3 | PNP Transistor, (To-220); Model No. MJE2955T |
| Q2 | NPN Transistor, (To-92); Model No. 2N3904 |
| Q1,4 | PNP Transistor, (To-92); Model No. 2N3906 |
| C8 | Capacitor, 0.33 microfarad |
| C5 | Capacitor, 10 microfarad |
| C1,2,3,4,9 | Capacitor, 0.1 microfarad |
| R10 | Resistor, 560 K ohm, ¼ w |
| R4,7 | Resistor, 50 ohm, ¼ w |
| R2 | Resistor, 10 K ohm, ¼ w |
| R1,3,5,6 | Resistor 1 K ohm, ¼ w |
| Y1 | Crystal, 14 PIN DIP, 2MHZ |
| SW1,2 | Dipswitch, 16 PIN |
| RP1,2 | Resistor Pack 2K, 10 PIN SIP |
| U6,7,8,9 | I.C., 14 PIN DIP, Quad 2 Input Hand buffer, Model No. 138 |
| U3,4,5 | I.C., 14 PIN DIP, Hex Inverter, Model No. 104 |
| U2 | I.C., 40 PIN DIP, Microprocessor, Rockwell, Model No. 6500/1EB1 |
| U1 | I.C., 8 PIN DIP Timer, Model No. LM555 |

Microcomputer ports A and B control polarity and duration of power applied to the thermoelectric tiles, 22a-22b. The polarity of the power determines whether a given surface of a tile gets hot or cold. Each port contains eight bits and each bit is assigned for the control of a single tile, 22A-22b respectively. Port A controls whether tiles are powered or not, while port B determines whether tile surfaces that are in contact with skin get hot or cold when powered. Bit No. 0 of ports A and B (PA0, PB0 in FIG. 5B) controls tile 22a; bit No. 1 controls tile 22a; and so forth. The logic gates U6–U9 (2 input NANDs with open collector outputs) are arranged so that either both power transistors Q3-0 through Q3-7 and Q5-0 through Q5-7 in FIGS. 5B and 5C which are connected together in push-pull are turned OFF in which case the respective tile is not active, or one or the other of the transistors (i.e. Q3-0 through Q3-7 or Q5-0 through Q5-7) is turned ON in which case the respective tile heats up or cools down. Under no conditions are both transistors turned ON as this would short out the power supplies.

It is believed that the programming of the microprocessor 12 is within the skill of one ordinarily skilled in the art given this disclosure.

While the invention has been described with reference to the preferred embodiment thereof it will be appreciated by those of ordinary skill in the art that various modifications can be made to the parts and elements that comprise the invention without departing from the spirit and scope of the invention as a whole.

We claim:

1. An apparatus for treating pain by creating a series of temperature patterns in a sequence on the kin adjacent the pain, said apparatus comprising:
   a plurality of spatially separated, thermoelectric means for producing a temperature change in said skin adjacent to the pain in response to an electrical input;
   electronic controller means connected to said plurality of thermoelectric means for independently controlling each of said thermoelectric means so that said plurality of thermoelectric means creates changeable temperature patterns in a sequence on said adjacent skin; and,
   delay time control means for producing a delay of at least sixty seconds between temperature patterns in a given sequence before a reversal of temperature gradient for said thermoelectric means,
   wherein said temperature patterns in a sequence and said delay of at least sixty seconds reduce the sensation of pain by minimizing adaptation.

2. The apparatus of claim 1 further comprising:
   program selector means connected to said electronic controller means for selecting at least one pattern from a plurality of possible patterns for reproduction by said plurality of thermoelectric means.

3. The apparatus of claim 2 wherein said thermoelectric means comprises a means that can become hot and cold from an intermediate base line temperature.

4. The apparatus of claim 3 wherein said thermoelectric means comprises Peltier-effect means.

5. The apparatus of claim 4 further comprising:
   hot intensity control means connected to said electronic controller means for controlling the hot intensity of said thermoelectric means; and,
   cold intensity control means connected to said electronic controller means for controlling the cold intensity of said thermoelectric means.

6. The apparatus of claim 5 wherein at least one of said plurality of thermoelectric means is off during any given pattern sequence so as to produce the effect of a moving pattern of temperature change.

7. The apparatus of claim 6 wherein said electronic controller means comprises a programmable microcomputer which continuously scans the setting of said program selector means thereby causing said thermal patterns to change in a repeatable series.

8. The apparatus of claim 7 wherein at least one Peltier-effect means alternates between an on and off condition while at least one other Peltier-effect means alternates in an opposite direction between an off and on position respectively.

9. An apparatus for treating pain by creating a series of changeable temperature patterns in a sequence on the skin adjacent to the pain, said apparatus comprising:
   a plurality of spatially separated, thermoelectric means for producing a temperature change in said skin adjacent to said pain in response to an electrical input, said plurality of thermoelectric means comprising at least four (4) Peltier-effect thermoelectric devices;
   electronic controller means connected to said Peltier-effect thermoelectric devices for independently controlling each of said Peltier-effect thermoelectric devices so that said Peltier-effect thermoelectric devices create changeable patterns of temperature in a sequence on said skin adjacent said pain; and,
   delay time control means for producing a delay of at least sixty seconds between temperature patterns in a given sequence before a reversal of temperature gradient for any of said Peltier-effect thermoelectric means,
   wherein said changeable temperature patterns in a sequence and said delay of at least sixty seconds reduce the sensation of pain by minimizing adaptation.

10. The apparatus of claim 9 further comprising:
    program selector means connected to said electronic controller means for selecting at least one temperature pattern in a sequence from a plurality of possible temperature patterns in a sequence for reproduction by said Peltier-effect thermoelectric devices and for stringing at least two different temperature patterns in a sequence together to form a series of different temperature pattern in a sequence on said skin adjacent the pain.

11. The apparatus of claim 10 further comprising:
hot intensity control means connected to said electronic controller means for controlling the hot intensity of said Peltier-effect thermoelectric devices; and,
cold intensity control means connected to said electronic controller means for controlling the cold intensity of said Peltier-effect thermoelectric devices,
wherein at least one of said Peltier-effect thermoelectric devices is OFF during any given sequence so as to produce the effect of a moving pattern of temperature change and wherein at least one Peltier-effect thermoelectric device alternates between an ON and OFF condition while at least one other Peltier-effect thermoelectric device alternates in an opposite direction between an OFF and ON position respectively.

12. A method of treating pain by creating a series of temperature patterns in a sequence on the skin adjacent to the pain, said method comprising the steps of:
(a) placing a plurality of temperature changeable, spatially separated, thermoelectric means on said skin adjacent to said pain;
(b) independently varying the temperature of each thermoelectric means to produce changeable temperature patterns in a sequence on said skin adjacent the pain;
(c) introducing a delay of at least sixty seconds between temperature patterns in a given sequence before a reversal of temperature gradient for any given thermoelectric means; and,
(d) repeating steps (b) and (c) above,
wherein said changeable temperature patterns in a sequence and said delay of at least sixty seconds reduce the sensation of pain by minimizing adaptation.

13. The method of claim 12 wherein said temperature changeable thermoelectric means comprises a Peltier-effect thermoelectric device capable of temperature change to hot and cold from an intermediate base line temperature, said method further comprising the steps of:
(e) varying the heating of said Peltier-effect thermoelectric device above said intermediate base line temperature; and,
(f) varying the cooling of said Peltier-effect thermoelectric device below said intermediate base line temperature.

14. The method of claim 13 wherein said varying of the temperature of said temperature changeable thermoelectric means produces a pattern of temperature change that simulates a wave.

15. The method of claim 13 wherein said array of temperature changeable thermoelectric means comprise at least four Peltier-effect thermoelectric devices arranged approximately in the shape of a rectangle and wherein said varying pattern of temperature change simulates a checker board pattern.

16. The method of claim 13 wherein said plurality of temperature change thermoelectric means comprises at least four Peltier-effect thermoelectric devices arranged in the shape of a rectangle and wherein said varying pattern of temperature change comprises a pattern which in at least two Peltier-effect thermoelectric devices on one side of said rectangle have a higher temperature than at least two Peltier-effect thermoelectric devices on the other side of said rectangle.

17. The method of claim 13 wherein said varying of the temperature of said temperature changeable thermoelectric means produces a random pattern.

18. The method of claim 13 wherein said varying of the temperature of said temperature changeable thermoelectric means produces a pattern of change that simulates two waves.

* * * * *